(12) United States Patent
Klatt et al.

(10) Patent No.: US 6,906,210 B2
(45) Date of Patent: Jun. 14, 2005

(54) METHOD FOR PRODUCING LIPOIC ACID AND DIHYDROLIPOIC ACID

(75) Inventors: Martin Jochen Klatt, Bad Dürkheim (DE); Markus Niebel, Mannheim (DE); Joachim Paust, Neuhofen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 106 days.

(21) Appl. No.: 10/343,034

(22) PCT Filed: Jul. 24, 2001

(86) PCT No.: PCT/EP01/08523

§ 371 (c)(1),
(2), (4) Date: Jan. 27, 2003

(87) PCT Pub. No.: WO02/10151

PCT Pub. Date: Feb. 7, 2002

(65) Prior Publication Data

US 2004/0044227 A1 Mar. 4, 2004

(30) Foreign Application Priority Data

Aug. 2, 2000 (DE) .......................................... 100 38 038
Sep. 5, 2000 (DE) .......................................... 100 44 000

(51) Int. Cl.[7] .............................................. C07B 45/00
(52) U.S. Cl. .......................................... 554/87; 554/85
(58) Field of Search ..................... 554/85, 87

(56) References Cited

U.S. PATENT DOCUMENTS

| | | |
|---|---|---|
| 2,788,355 A | 4/1957 | Bullock |
| 3,132,152 A | 5/1964 | Ohara et al. |
| 5,281,722 A | 1/1994 | Blaschke et al. |
| 5,380,920 A | 1/1995 | Paust et al. |
| 5,530,143 A | 6/1996 | Balkenhohl et al. |
| 5,731,448 A | 3/1998 | Gewald et al. |

FOREIGN PATENT DOCUMENTS

| | | |
|---|---|---|
| DE | 42 29 914 | 3/1994 |
| EP | 487 986 | 6/1992 |
| EP | 543 088 | 5/1993 |
| EP | 763 533 | 3/1997 |
| GB | 996703 | 6/1965 |
| WO | 00/08012 | 2/2000 |

OTHER PUBLICATIONS

XP–002188279, Reed et al.
XP 002022470, Acker et al.
XP 002197086, Gunsalus et al.
XP002197089.
XP–002197091.
A Short and Productive Synthesis . . . Bringmann et al.655–661.
J.Sci.&Ind.Res., vol. 49, 8/90,400–409, Yadav et al.
Tet.Ltr.vol. 30, No. 42,pp. 57–55708.
Chem.Soc.Perkin Trans.1988, Brookes et al, 9–12.
The Synthesis of (R)—(+)Lipoic . . . , Adger et al., 253–261, Bio.Med.Chem., vol. 5,No 2, 1997.
J.Chem.Soc.,Chem,1983, Brookes et al.,1051–1053.
Abst.JP 1960–35704.
XP–002197090.
XP–002197087.
XP–002197088.

*Primary Examiner*—Deborah D. Carr
(74) *Attorney, Agent, or Firm*—Novak Druce & Quigg, LLP

(57) ABSTRACT

Processes for the preparation of R-lipoic acid or S-lipoic acid comprising a process step selected from
 a) distillation of dihydrolipoic acid,
 b) reaction of

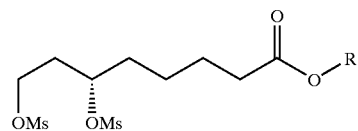

or its stereoisomer, where Ms is $SO_2$—R' and R and R' independently of one another is [sic] $C_1$–$C_6$-alkyl, $C_3$–$C_8$-cycloalkyl, $C_3$–$C_8$-cycloalkylalkyl, aryl or aralkyl, with sodium sulfide and sulfur in ethanol and reaction with a complex hydride,
 (c) the extraction of a protic solution of R-dihydrolipoic acid or S-dihydrolipoic acid with organic solvents at a pH from 9 to 10, or
 (d) the extraction of R-dihydrolipoic acid or S-dihydrolipoic acid with organic solvents from a protic solution at a pH of 4 to 5, or a combination of one or more of steps (a) to (d), and processes for the preparation of dihydrolipoic acid and the compound 1,6,8 [lacuna] octanetriol.

21 Claims, No Drawings

METHOD FOR PRODUCING LIPOIC ACID AND DIHYDROLIPOIC ACID

The invention relates to processes for the preparation of R- and S-lipoic acid and R- and S-dihydrolipoic acid.

The invention especially relates to processes for preparing pure R- or S-dihydrolipoic acid, which is either used directly or processed further to give R- and S-lipoic acid.

Dihydrolipoic acid and lipoic acid are naturally occurring substances which have particular importance in cell metabolism. As a coenzyme, e.g. of pyruvate dehydrogenase, R-lipoic acid plays a central role in energy production. To fully display its very good antioxidative properties, R-lipoic acid is activated to dihydrolipoic acid in the metabolism. As they can be converted into one another in vivo, dihydrolipoic acid and lipoic acid can be used for the same fields of use. R-Lipoic acid positively affects age-related changes in the metabolism and is therefore also of interest in the cosmetic area.

Lipoic acid and dihydrolipoic acid can be employed as a nutraceutical in the foodstuffs area.

Use of dihydrolipoic acid and/or lipoic acid as pharmacons is also possible.

It is known that R-lipoic acid increases sensitivity to insulin and can thus be used as an antidiabetic, and also for the prevention and alleviation of diabetic late damage.

Various methods for the preparation of optically pure R- and S-lipoic acid or dihydrolipoic acid are known from the literature:

G. Bringmann, D. Herzberg, G. Adam, F. Balkenhohl, J. Paust Z. Naturforschung 1999, 54b, 665–661;
B. Adger et al. Bioorg. Med. Chem. 1997, 5, 253–61;
J. S. Yadav, S. Mysorekar, K. Garyali J. Scientific & Industrial Res. 1990, 49, 400–409;
A. S. Gopalan, H. K. Jacobs Tetrahedron Lett 1989, 42, 5705;
M. H. Brookes, B. T. Golding, A. T. Hudson Perkin Transaction I, 1988, 9–12;
M. H. Brookes, B. T. Golding, D. A. Howes, A. T. Hudson Chemical Communication 1983, 1051–53;
JP 1960-35704; EP 543088; EP 487 986.

Thus enantiomerically pure lipoic acid and dihydrolipoic acid can be prepared in various ways such as chemical or enzymatic cleavage of the racemates, with the aid of chiral templates, or by enantioselective synthesis or microbiological transformation.

The published syntheses either proceed via many steps and/or use expensive starting materials or reaction conditions. The known processes are deserving of improvement with respect to yield, environmental and/or cost considerations. Since lipoic acid and dihydrolipoic acid are also intended to be employed in humans, products which are as pure as possible and which can be prepared simply in high yields are desired.

The syntheses of R-lipoic acid and R-dihydrolipoic acid are described by way of example below. Analogously, the S-enantiomers can also be prepared in each case.

Bringmann et al. proposed two synthesis routes for R-lipoic acid which starts from chiral 6,8-dihydroxyoctanoic acid esters (1)

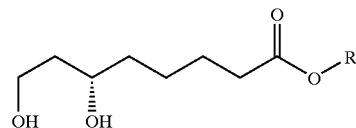

The yields of lipoic acid with respect to (1) are 65%; in the case of the introduction of S using KSAc, however, the material obtained only has a GC purity of 98%, which could be problematical for human applications.

Alternatively, according to Bringmann et al. the introduction of sulfur can take place in DMF using NaS+S, the subsequent hydrolysis being able to take place using lipase or potassium carbonate. The methyl lipoate obtained is very sensitive to polymerization.

Surprisingly, it has now been found that by reaction of the sulfonic acid derivatives, for example of the mesylate

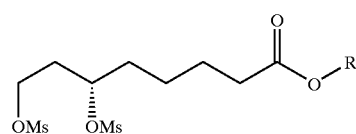

where Ms is —$SO_2$—R' and R and R' independently of one another is [sic] $C_1$–$C_6$-alkyl, $C_3$–$C_8$-cycloalkyl, $C_3$–$C_8$-cycloalkylalkyl, aryl or aralkyl, preferably methyl, with sodium sulfide and sulfur in ethanol and subsequent reaction with a complex hydride, pure dihydrolipoic acid

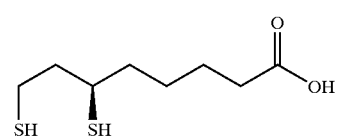

can be prepared. Preferably, this reaction is carried out without isolation of the intermediates.

The preferred meaning for Ms is mesylate or tosylate.

By means of the process according to the invention, a higher chemical purity of R- or S-lipoic acid is achieved in comparison with the process described in EP 487 986.

The compound (2) is prepared, for example, by reaction of the corresponding alkyl 6,8-dihydroxyoctanoate (1) with triethylamine and mesyl chloride. The preferred alkyl esters are $C_1$–$C_6$-alkyl; methyl is particularly preferred.

Aryl or Ar in aralkyl is preferably phenyl, or naphthyl which can in each case be substituted by one, two or three $C_1$–$C_4$-alkyl radicals; "alkyl" in aralkyl or cycloalkylalkyl is preferably $C_1$–$C_4$-alkyl, particularly preferably —$CH_2$—.

The reaction of the sulfonic acid derivatives 2 [sic], for example of the mesylate, is preferably carried out in an ethanolic $Na_2S$/S mixture having a content of over 90% by weight of EtOH, particularly preferably having a content of over 95% by weight of ethanol. The ethanolic mixture preferably contains at least equimolar amounts of $Na_2S$, S and mesylate and at most one molar excess each of 100% strength $Na_2S$ and S based on mesylate. A 25 to 35% molar excess of $Na_2S$ and a 45 to 55% molar excess of sulfur is preferred. The ethanolic $Na_2S$ mixture is preferably boiled beforehand.

Complex hydrides are preferably understood as meaning borohydrides, in particular alkali metal borohydrides such as $NaBH_4$.

The reaction with complex hydrides is preferably carried out in alkaline solution, particularly in concentrated alkali metal hydroxide solution. A borol solution (12% strength $NaBH_4$ in 14 M NaOH) is particularly preferred.

If the mixture is then acidified (pH<2) and extracted with an organic solvent (preferably ethyl acetate or toluene), dihydrolipoic acid is obtained in high yield.

If the dihydrolipoic acid thus obtained is oxidized to lipoic acid and crystallized, very pure lipoic acid is obtained in high yield (GC>99.5%, ee HPLC (CSP)>99% (detection limit)). The oxidation can be carried out using $FeCl_3$/air, the crystallization preferably in heptane/toluene (WO 00/08012).

Surprisingly, dihydrolipoic acid can be distilled without significant decomposition in a temperature range from 160 to 220° C., preferably even at 180 to 210° C., particularly preferably at 200° C.±5° C., at pressures from 0.5 to 5 mbar, particularly preferably at 1 to 3 mbar. The distillation is preferably carried out continuously (Sambay, falling film or thin-layer-evaporator). This pressure range can be achieved industrially without significant expenditure. Surprisingly, after subsequent oxidation and crystallization over 10% more lipoic acid can be obtained from the dihydrolipoic acid than without distillation. A further optimization of the purification of the dihydrolipoic acid surprisingly led, although more steps were inserted, to higher yields of pure lipoic acid.

If, after the reaction of the mixture with a complex hydride, the protic solution of dihydrolipoic acid is extracted with an organic solvent at a pH of 9 to 10, preferably at 9.5, a greater yield of crystallizate is obtained after work-up to give lipoic acid. If the protic solution of dihydrolipoic acid is extracted in organic solvent at a pH of 4 to 5, preferably at 4.5, a greater yield of crystallizate is obtained after work-up to give lipoic acid.

If extraction is carried out in an organic solvent before the work-up to give lipoic acid (optimal distillation and oxidation with crystallization), the yield of lipoic acid and the purity of dihydrolipoic acid are increased.

The steps in processes for the purification of dihydrolipoic acid indicated above lead individually and in combination to higher yields of crystallized lipoic acid. The combination of individual steps is preferred; carrying out all abovementioned process steps, especially in the order as in Example 4, is very particularly preferred.

It has surprisingly been found that the reversal of the extraction steps (first extraction at a pH from 4 to 5 and subsequent purification at a pH from 9 to 10) enables high yields of lipoic acid crystallizate to be obtained even without distillation of the dehydrolipoic acid. The procedure is likewise particularly preferred.

Protic solutions are understood as meaning solvent mixtures containing at least 30% of water, preferably more than 50% of water, particularly preferably more than 75% of water. The other components are polar solvents such as DMF or alcohols, in particular ethanol. Organic solvents for the extraction are preferably apolar solvents, e.g. halogenated solvents such as methylene chloride or chloroform, glycol ethers, ethers such as diethyl ether or methyl t-butyl ether, esters such as ethyl acetate, aliphatic and aromatic hydrocarbons such as cyclohexane, hexane, heptane, toluene, or mixtures thereof, the preferred solvents being hexane, heptane, toluene and ethyl acetate.

Pure lipoic acid or pure dihydrolipoic acid is understood as meaning chemically and in particular enantiomerically pure lipoic acid or dihydrolipoic acid respectively.

R- or S-dihydrolipoic acid and R-lipoic acid or S-lipoic acid is understood as meaning material which preferably has an enantiomeric purity (ee value determined by HPLC, CSP) of greater than/equal to 70%, preferably 80%, particularly preferably 90%, very particularly preferably 95%, even more preferably 97% or 98%, most preferably 99% and greater, i.e. lying at the detection limit.

With respect to the chemical purity (GC or HPLC), R- or S-dihydrolipoic acid is material preferably having a purity of greater than or equal to 80%, particularly preferably greater than or equal to 90%, very particularly preferably greater than or equal to 95% and 97% respectively.

With respect to the chemical purity of R- or S-lipoic acid, material having greater than 99%, particularly preferably greater than 99.5%, very particularly preferably greater than 99.9%, is preferred. This corresponds to the detection limit of the methods used.

The invention additionally relates to the further processing of R-lipoic acid or S-lipoic acid obtained by the processes of the invention in pharmacologically acceptable derivatives such as esters or amides of lipoic acid. The reaction and derivatives are known from the literature. The invention further relates as well to the further processing of the R- or S-lipoic acid prepared in accordance with the invention into pharmacologically acceptable salts, such as alkali metal salts and alkaline earth metal salts or, for example, the trometamol salt of R-lipoic acid.

In addition, the invention relates to a novel optically active trithiol of the formula

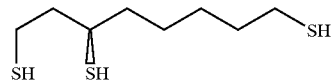

and its stereoisomer.

1,6,8-Octanetrithiol is formed from 1,6,8-octanetriol on the introduction of sulfur. The triol is a secondary component of the diol (1). It is concentrated in the organic phase during the extraction at pH 9 and can be isolated therefrom. The octanetrithiol can be employed as an optically active synthesis unit and as a selective catalyst poison.

The following examples illustrate the invention without restricting it.

EXAMPLE 1

(a) (1→2): 170 ml (1.25 mol) of triethylamine and a solution of 98 g (97%, 0.5 mol) of methyl (6S)-6,8-dihydroxyoctanoate 1 are initially introduced into 1 liter of toluene. The mixture is cooled and 143 g (1.25 mol) of mesyl chloride are added. After removal of the triethylammonium hydrochloride, the solution is concentrated. The conversion is quantitative.

(b) (2→3): 151 g (0.63 mol) of sodium sulfide and 24 g of sulfur powder are boiled in ethanol. The reaction mixture is treated with 0.5 mol of the mesylate. It is diluted with completely deionized water (CD water). After reaction with 174 g (0.55 mol) of 12% $NaBH_4$ solution in 14 M sodium hydroxide solution (borol solution), the solvent is distilled off. The mixture is adjusted to pH 1 and extracted with toluene. Yield: 105.1 g (90%, 91% with respect to diol 1)

(c) (3→4): 105.1 g of dihydrolipoic acid in 5 liters of CD water are stirred into a 10 liter round-bottomed flask, and the solution is adjusted to pH 8.5 and treated with catalytic amounts of Fe(III) chloride. The mixture is aerated with air until conversion is complete. The solution is adjusted to pH 2 and extracted with toluene. The phases are separated and the organic phase is concentrated. The residue is treated with technical heptane and forced through a filter charged with 5 g of silica gel.

On cooling, R-lipoic acid crystallizes out and is dried in a stream of nitrogen. The yield is 65.9 g (64% of theory with respect to diol 1).

GC content:>99.9%
ee content:>99%

EXAMPLE 2

Introduction of the Distillation (a) (1→2): 170 ml (1.25 mol) of triethylamine and a solution of 98 g (97%, 0.5 mol) of methyl (6S)-6,8-dihydroxyoctanoate 1 are introduced into 1 liter of toluene. The mixture is cooled and 143 g (1.25 mol) of mesyl chloride are added. After separation of the triethylammonium hydrochloride, the solution is concentrated. The conversion is quantitative.

(b) (2→3): 151 g (0.63 mol) of sodium sulfide and 24 g of sulfur powder are boiled in ethanol. The reaction mixture is treated with 0.5 mol of the mesylate. It is diluted with CD water, 174 g (0.55 mol) of borol solution are added and the solvent is distilled off. The mixture is adjusted to pH 1 and extracted with toluene. The organic phase is freed from the solvent. The residual oil is distilled in a falling-film evaporator (1 to 3 mbar, 200° C.). Yield: 95.3 g (96% strength, 88% with respect to diol 1).

(c) (3→4): 95.3 g of distilled dihydrolipoic acid in 5 liters of CD water are stirred in a 10 liter round-bottomed flask, and the solution is adjusted to pH 8.5 and treated with catalytic amounts of Fe(III) chloride. The mixture is aerated with air until conversion is complete. The solution is adjusted to pH 2 and extracted with toluene. The phases are separated and the organic phase is concentrated. The residue is treated with technical heptane and forced through a filter charged with 5 g of silica gel.

On cooling, R-lipoic acid crystallizes out and is dried in a stream of nitrogen. The yield is 74.2 g (72% of theory with respect to diol 1).

GC content:>99.9%
ee content:>99%

EXAMPLE 3

Extraction at pH 9 and Distillation (a) (1→2): 170 ml (1.25 mol) of triethylamine and a solution of 98 g (97%, 0.5 mol) of methyl (6S)-6,8-dihydroxyoctanoate 1 are introduced into 1 liter of toluene. The mixture is cooled and 143 g (1.25 mol) of mesyl chloride are added. After separation of the triethylammonium hydrochloride, the solution is concentrated. The conversion is quantitative.

(b) (2→3): 151 g (0.63 mol) of sodium sulfide and 24 g of sulfur powder are boiled in ethanol. The reaction mixture is treated with 0.5 mol of the mesylate. It is diluted with CD water and 174 g (0.55 mol) of borol solution are added. The mixture is adjusted to pH 9 using sulfuric acid and extracted with toluene. The toluene phase is discarded. The mixture is then adjusted to pH 1 and extracted with toluene. The organic phase is freed from the solvent. The residual oil is distilled in a falling-film evaporator (1 to 3 mbar, 200° C.). Yield: 91.1 g (95%, 85% with respect to diol 1).

(c) (3→4): 91.1 g of distilled dihydrolipoic acid in 5 liters of CD water are stirred in a 10 liter round-bottomed flask, and the solution is adjusted to pH 8.5 and treated with catalytic amounts of Fe(III) chloride. The mixture is aerated with air until conversion is complete. The solution is adjusted to pH 2 and extracted with toluene. The phases are separated and the organic phase is concentrated. The residue is treated with technical heptane and forced through a filter charged with 5 g of silica gel.

On cooling, R-lipoic acid crystallizes out and is dried in a stream of nitrogen. The yield is 76.2 g (74% of theory with respect to diol 1)

GC content:>99.9%
ee content:>99%

EXAMPLE 4

Extractions at pH 9, pH 4 and Distillation (a) (1→2): 170 ml (1.25 mol) of triethylamine and a solution of 98 g (97%, 0.5 mol) of methyl (6S)-6,8-dihydroxyoctanoate 1 are introduced into 1 liter of toluene. The mixture is cooled and 143 g (1.25 mol) of mesyl chloride are added. After separation of the triethylammonium hydrochloride, the solution is concentrated. The conversion is quantitative.

(b) (2→3): 151 g (0.63 mol) of sodium sulfide and 24 g of sulfur powder are boiled in ethanol. The reaction mixture is treated with 0.5 mol of the mesylate. It is diluted with CD water and 174 g (0.55 mol) of borol solution are added. The mixture is adjusted to pH 9 using sulfuric acid and extracted with toluene. The toluene phase is discarded. The mixture is then adjusted to pH 4 and extracted with toluene. The organic phase is freed from solvent. The residual oil is distilled in a falling-film evaporator (1 to 3 mbar, 200° C.). Yield: 95.2 g (97%, 88% with respect to diol 1).

(c) (3→4): 95.2 g of distilled dihydrolipoic acid in 5 liters of CD water are stirred in a 10 liter round-bottomed flask, and the solution is adjusted to pH 8.5 and treated with catalytic amounts of Fe(III) chloride. It is aerated with air until conversion is complete. The solution is adjusted to pH 2 and extracted with toluene. The phases are separated and the organic phase is concentrated. The residue is treated with technical heptane and forced through a filter charged with 5 g of silica gel.

On cooling, R-lipoic acid crystallizes out and is dried in a stream of nitrogen. The yield is 77.2 g (75% of theory with respect to diol 1)

GC content:>99.9%
ee content:>99%

EXAMPLE 5

Extractions at pH 9 and pH 4

(a) (1→2): 170 ml (1.25 mol) of triethylamine and a solution of 98 g (97%, 0.5 mol) of methyl (6S)-6,8-dihydroxyoctanoate 1 are introduced into 1 liter of toluene. The mixture is cooled and 143 g (1.25 mol) of mesyl chloride are added. After separation of the triethylammonium hydrochloride, the solution is concentrated. The conversion is quantitative.

(b) (2→3): 151 g (0.63 mol) of sodium sulfide and 24 g of sulfur powder are boiled in ethanol. The reaction mixture is treated with 0.5 mol of the mesylate. It is diluted with CD water and 174 g (0.55 mol) of borol solution are added. The mixture is adjusted to pH 4 using sulfuric acid and extracted with toluene. The toluene phase is discarded. The mixture is then adjusted to pH 9 and extracted with toluene. The organic phase is discarded.

(c) (3→4): The aqueous solution obtained is stirred up with CD water to 5 liters, the batch is treated with catalytic amounts of Fe(III) chloride. It is aerated with air until conversion is complete. The solution is adjusted to pH 2 and extracted with toluene. The phases are separated and the organic phase is concentrated. The residue is treated with technical heptane and forced through a filter charged with 5 g of silica gel.

On cooling, R-lipoic acid crystallizes out and is dried in a stream of nitrogen. The yield is 73% of theory with respect to diol 1

GC content:>99.9%
ee content:>99%

What is claimed is:

1. A process for the preparation of R-lipoic acid or S-lipoic acid comprising
reaction of

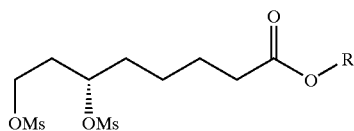

or its stereoisomer, where Ms is $SO_2$—R', and R and R' independently of one another are $C_1$–$C_6$-alkyl, $C_3$–$C_8$-cycloalkyl, $C_3$–$C_8$-cycloalkylalkyl, aryl or aralkyl, with sodium sulfide and sulfur in ethanol and reaction with a complex hydride.

2. A process as claimed in claim 1, comprising a process step selected from
extraction of a protic solution of R-dihydrolipoic acid or S-dihydrolipoic acid with organic solvents at a pH of 9 to 10, or
extraction of R-dihydrolipoic acid or S-dihydrolipoic acid with organic solvents from a protic solution at a pH of 4 to 5,
distillation of the dihydrolipoic acid
or a combination of one or more of the steps.

3. A process as claimed in claim 2, in which the distillation of R-dihydrolipoic acid or S-dihydrolipoic acid is carried out at a pressure of 0.5 to 5 mbar.

4. A process as claimed in claim 1 comprising the extraction of R-dihydrolipoic acid or S-dihydrolipoic acid with organic solvents from a protic solution at a pH of 4 to 5 and the extraction of a protic solution of R-dihydrolipoic acid or S-dihydrolipoic acid with organic solvents at a pH of 9 to 10.

5. A process as claimed in claim 1 comprising the extraction of a protic solution of R-dihydrolipoic acid or S-dihydrolipoic acid with organic solvents at a pH of 9 to 10 and the extraction of R-dihydrolipoic acid or S-dihydrolipoic acid with organic solvents from a protic solution at a pH of 4 to 5.

6. A process as claimed in claim 1 and subsequent distillation of R-dihydrolipoic acid or S-dihydrolipoic acid at a pressure of 1 to 3 mbar at temperatures between 180° C. and 220° C.

7. A process as claimed in claim 1, the organic solvent being apolar.

8. A process as claimed in claim 1, the apolar solvent being toluene.

9. A process for the preparation of pure R-dihydrolipoic acid or S-dihydrolipoic acid comprising processes as claimed in claim 1.

10. A process for the preparation of pharmacologically tolerable salts or derivatives of R-lipoic acid or S-lipoic acid, R- or S-lipoic acid obtained as claimed in claim 1 being reacted.

11. A compound of the formula

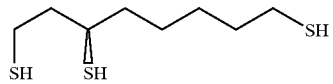

and its steroisomers.

12. A process for the preparation of R-lipoic acid or S-lipoic acid comprising a process step selected from
extraction of a protic solution of R-dihydrolipoic acid or S-dihydrolipoic acid with organic solvents at a pH of 9 to 10, or
extraction of R-dihydrolipoic acid or S-dihydrolipoic acid with organic solvents from a protic solution at a pH of 4 to 5,
or combination of these steps.

13. A process as claimed in claim 12, comprising a process step selected from
reaction of

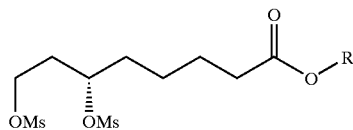

or its stereoisomer, where Ms is $SO_2$—R', and R and R' independently of one another are $C_1$–$C_6$-alkyl, $C_3$–$C_8$-cycloalkyl, $C_3$–$C_8$-cycloalkylalkyl, aryl or aralkyl, with sodium sulfide and sulfur in ethanol and reaction with a complex hydride,
distillation of the dihydrolipoic acid.

14. A process as claimed in claim 13, in which the distillation of R-dihydrolipoic acid or S-dihydrolipoic acid is carried out at a pressure of 0.5 to 5 mbar.

15. A process as claimed in claim 12 comprising the extraction of R-dihydrolipoic acid or S-dihydrolipoic acid with organic solvents from a protic solution at a pH of 4 to 5 and the extraction of a protic solution of R-dihydrolipoic acid or S-dihydrolipoic acid with organic solvents at a pH of 9 to 10.

16. A process as claimed in claim 12 comprising the extraction of a protic solution of R-dihydrolipoic acid or S-dihydrolipoic acid with organic solvents at a pH of 9 to 10 and the extraction of R-dihydrolipoic acid or S-dihydrolipoic acid with organic solvents from a protic solution at a pH of 4 to 5.

17. A process as claimed in claim 12 and subsequent distillation of R-dihydrolipoic acid or S-dihydrolipoic acid at a pressure of 1 to 3 mbar at temperatures between 180° C. and 220° C.

18. A process as claimed in claim 12, the organic solvent being apolar.

19. A process as claimed in claim 12, the apolar solvent being toluene.

20. A process for the preparation of pure R-dihydrolipoic acid or S-dihydrolipoic acid comprising processes as claimed in claim 12.

21. A process for the preparation of pharmacologically tolerable salts or derivatives of R-lipoic acid or S-lipoic acid, R-lipoic acid or S-lipoic acid obtained as claimed in claim 12 being reacted.

* * * * *